United States Patent
Goeders et al.

(10) Patent No.: US 10,302,974 B2
(45) Date of Patent: May 28, 2019

(54) PREPARATION CELL SYSTEMS AND METHODS OF PREPARING A STATE OF LASER LIGHT

(71) Applicant: Honeywell International Inc., Morris Plains, NJ (US)

(72) Inventors: James Goeders, Plymouth, MN (US); Matthew Edward Lewis Jungwirth, Golden Valley, MN (US)

(73) Assignee: Honeywell International Inc., Morris Plains, NJ (US)

( * ) Notice: Subject to any disclaimer, the term of this patent is extended or adjusted under 35 U.S.C. 154(b) by 11 days.

(21) Appl. No.: 15/584,456

(22) Filed: May 2, 2017

(65) Prior Publication Data

US 2017/0235163 A1 Aug. 17, 2017

Related U.S. Application Data

(63) Continuation of application No. 14/686,481, filed on Apr. 14, 2015, now Pat. No. 9,645,417.

(51) Int. Cl.

| G02F 1/01 | (2006.01) |
|---|---|
| G01N 21/64 | (2006.01) |
| H01J 49/42 | (2006.01) |
| G02F 1/035 | (2006.01) |
| G02F 1/11 | (2006.01) |
| G02F 1/125 | (2006.01) |
| H01S 3/00 | (2006.01) |
| G06N 10/00 | (2019.01) |

(Continued)

(52) U.S. Cl.
CPC ......... *G02F 1/0115* (2013.01); *G01N 21/645* (2013.01); *G02F 1/035* (2013.01); *G02F 1/11* (2013.01); *G02F 1/113* (2013.01); *G02F 1/125* (2013.01); *H01J 49/424* (2013.01); *H01S 3/0085* (2013.01); *G01N 2021/6484* (2013.01); *G01N 2201/067* (2013.01); *G06N 10/00* (2019.01); *G06N 99/002* (2013.01); *H01J 49/0018* (2013.01)

(58) Field of Classification Search
CPC ........ G02F 1/0115; G02F 1/035; G02F 1/113; G02F 1/125; G01B 21/645; H01S 3/0085; H01S 3/2316; G01N 2021/6484; G02B 6/266; B23K 26/0643
See application file for complete search history.

(56) References Cited

U.S. PATENT DOCUMENTS

| 7,180,078 B2 | 2/2007 | Pau et al. |
|---|---|---|
| 7,580,609 B1 | 8/2009 | Pannell |

(Continued)

OTHER PUBLICATIONS

Jungsang, et al., "Integrated Optical Approach to Trapped Ion Quantam Computation", Quantam Information and Computation, vol. 0 No. 0, 2003, 22 pp.

(Continued)

*Primary Examiner* — Akm E Ullah
(74) *Attorney, Agent, or Firm* — Brooks, Cameron & Huebsch, PLLC

(57) ABSTRACT

Preparation cell systems and methods are described herein. One example of a system for a preparation cell includes a laser coupled to a fiber bundle comprising a plurality of fibers, a preparation cell to prepare a state of laser light received by the fiber bundle, and an exiting fiber bundle coupled to the preparation cell.

20 Claims, 3 Drawing Sheets

(51) Int. Cl.
*G06N 99/00* (2019.01)
*H01J 49/00* (2006.01)

(56) References Cited

U.S. PATENT DOCUMENTS

| | | |
|---|---|---|
| 2002/0006731 A1 | 1/2002 | Nakano et al. |
| 2002/0168134 A1* | 11/2002 | Sundaram .............. B82Y 20/00 385/16 |
| 2006/0249491 A1* | 11/2006 | Jurgensen .......... B23K 26/0643 219/121.69 |
| 2010/0134869 A1 | 6/2010 | Bernet et al. |
| 2010/0177794 A1 | 7/2010 | Peng et al. |

OTHER PUBLICATIONS

Nagerl, et al., "Laser addressing of individual ions in a linear ion trap", Physical Review A, vol. 60, No. 1, Dec. 10, 1998, 4 pp.
Extended Search Report from Related European Patent Application No. 16154710, dated Sep. 6, 2016, 8 pp.

* cited by examiner

PREPARATION CELL SYSTEMS AND METHODS OF PREPARING A STATE OF LASER LIGHT

CROSS REFERENCE TO RELATED APPLICATION

This application is a divisional of U.S. application Ser. No. 14/686,481, filed Apr. 14, 2015, the entire specification of which is incorporated herein by reference.

STATEMENT OF GOVERNMENT RIGHTS

This invention was made with Government support under contract: W911NF-12-1-0605, awarded by the U.S. Army. The Government has certain rights in this invention.

TECHNICAL FIELD

The present disclosure relates to preparation cell systems and methods.

BACKGROUND

Atom traps (e.g., ion traps, neutral atom traps, etc.) can be utilized to isolate atoms for experimentation. For example, ion traps can use a combination of electrical and magnetic fields to capture an ion in a potential well. In this example, when an ion trapped in an ion trap is illuminated by a specific laser (e.g. when a laser beam is shined on the ion in the trap), the ion may fluoresce light. The light fluoresced from the ion can be detected by a detector.

Increasing the number of ion traps on a single die can be space limited due to on-chip filter capacitors and optically limited due to wire bonds in a beam path. In some previous approaches, a number of lasers may be linearly added when adding additional ions to address. Ion traps have a number of uses such as mass spectrometry, spectroscopy, basic physics research, and/or controlling quantum states.

DETAILED DESCRIPTION

Figure 1:
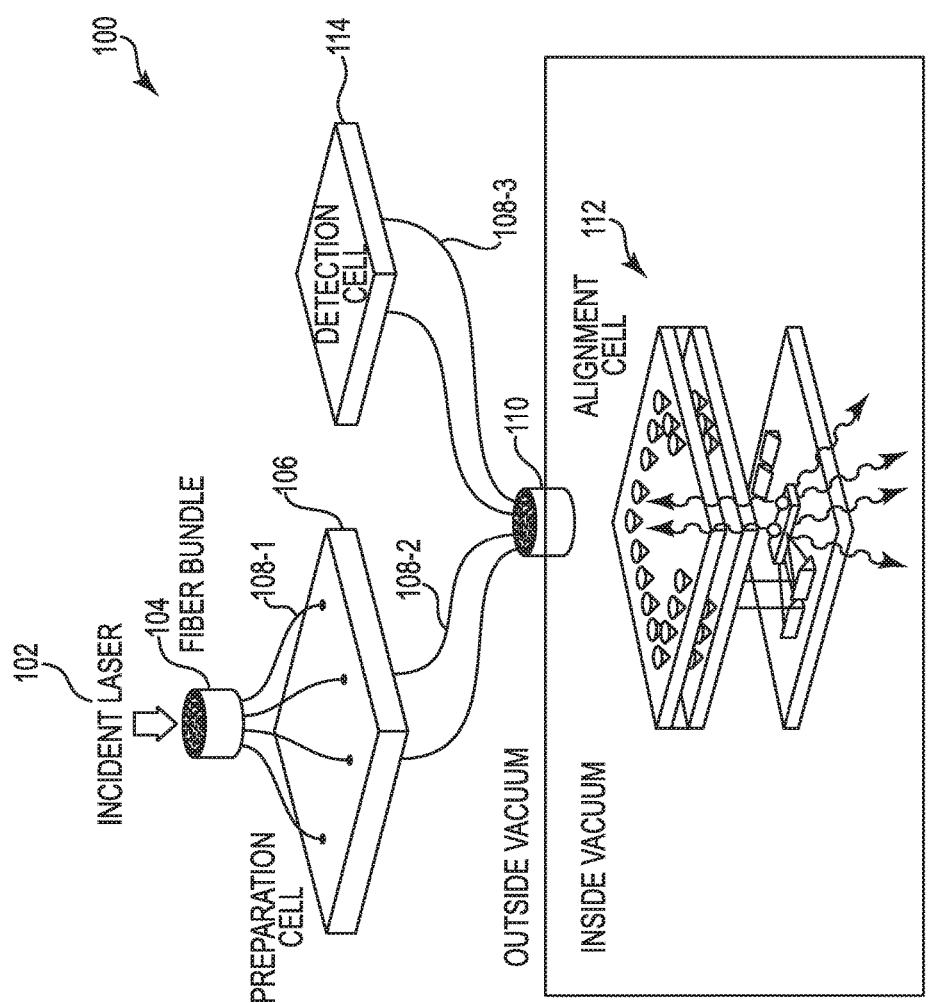
FIG. 1 illustrates an example of a preparation cell system in accordance with one or more embodiments of the present disclosure.

A number of preparation cell systems and methods are described herein. One example of a system for a preparation cell can include a laser coupled to a fiber bundle comprising a plurality of fibers, a preparation cell to prepare a state of laser light received by the fiber bundle, and an exiting fiber bundle coupled to a preparation cell. Another example of a system for a preparation cell can include a laser coupled to an electro-optical modulator (EOM), a fiber bundle comprising a plurality of fibers coupled to the EOM, a preparation cell to: set a frequency and polarization of laser light received by the plurality of fibers from the EOM and shutter the laser light received by the plurality of fibers from the EOM, and a vacuum port fiber bundle coupled to the alignment cell. Furthermore, an example a system for a preparation cell can include a laser coupled to a fiber bundle comprising a plurality of fibers, a preparation cell comprising a plurality of electro-optical modulators (EOMs), wherein each respective EOM is coupled to a different one of the plurality of fibers separated by the fiber bundle, and a vacuum port fiber bundle coupled to an alignment cell to receive the plurality of fibers.

The preparation cell systems described herein can be utilized in a single-ion addressing system. For example, the preparation cell system can be coupled to an alignment cell inside a vacuum chamber, and/or a detection cell. The alignment cell can include a plurality of ion traps and/or ion trapping zones within a single trap. In some embodiments, the alignment cell can utilize the preparation cell systems to split a laser source into a plurality of fibers that can be utilized for a number of the plurality of ion traps or zones. For example, a single laser source can be split from a fiber bundle into a plurality of fibers, have a state prepared by a preparation cell, and the plurality of fibers can be received by a vacuum port fiber bundle coupled to the alignment cell. In previous approaches, a plurality of lasers could be needed to simultaneously hit a number of ions located at a plurality of ion traps. For example, a plurality of additional lasers could be needed for each number of ions to be added.

In some embodiments, the laser may be a Doppler cooling laser (e.g., a laser used in a Doppler cooling mechanism), and in some embodiments the laser may be an operation laser (e.g., a laser used in Raman cooling, state preparation, EIT manipulation, and/or gate experiments, for instance). In both such embodiments, the laser may be a 369 nanometer (nm) laser. However, embodiments of the present disclosure are not limited to a particular type of laser.

The preparation cell systems described herein can be utilized to generate relatively large spacing sidebands for state preparation and addressing hyperfine transitions utilizing an electro-optical modulator (EOM) that is coupled to a number of the plurality of fibers. In addition, the preparation cell systems described herein can be utilized to set a frequency of the laser light and/or shutter the laser light utilizing an acousto-optic modulator (AOM) that is coupled to a number of the plurality of fibers. Furthermore, the preparation cell systems described herein can be utilized to set a polarization state of the laser light utilizing, for example, a Pockels cell coupled to a number of the plurality of fibers. In some embodiments, a plurality of tracks can be used within the preparation cell. Each of the plurality of tracks can include one or more of an EOM, AOM, and/or Pockels cell to prepare a state of the received laser light as described herein. The light from the preparation cell system can be sent to an alignment cell via a vacuum port fiber bundle coupled to the alignment cell. Ion traps are discussed herein as specific examples. However, specific implementations are not limited to only ion traps. That is, the preparation cell systems and methods can be utilized in combination with a number of different atom trap types.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that mechanical, electrical, and/or process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 104 may reference element "04" in FIG. 1, and a similar element may be referenced as 304 in FIG. 3.

As used herein, "a" or "a number of" something can refer to one or more such things. For example, "a number of lasers" can refer to one or more lasers.

FIG. 1 illustrates an example of a preparation cell system 100 in accordance with one or more embodiments of the present disclosure. The preparation cell system 100 can be utilized to prepare light from an incident laser 102 for utilization in an alignment cell 112.

The preparation cell system 100 can utilize a fiber bundle 104 to receive light from the incident laser 102. The fiber bundle 104 can be coupled to a plurality of tracks (e.g., multi-track, etc.) within a preparation cell 106 (e.g., fiber separator, fiber separator comprising an EOM, AOM, and/or Pockels Cell, etc.). In some embodiments, the incident laser 102 can be a collimated (e.g., accurately make rays of light or particles parallel) with a flat-top laser irradiance profile. In addition, the incident laser 102 can be the same diameter as the fiber bundle 104 to avoid light from the incident laser 102 from escaping an exterior portion of the fiber bundle 104.

The preparation cell 106 can receive a number of separated fibers 108-1 from the fiber bundle 104 coupled to the incident laser 102. In some embodiments, an electro-optical modulator (EOM) can be coupled to the incident laser 102 and the EOM can be coupled to the fiber bundle 104. The EOM can be coupled to the incident laser 102 when the incident laser 102 is a Doppler cooling (DC) laser or similar light source. In some embodiments the EOM can be a 7.37 gigahertz (GHz) EOM that prepares the state of the incident laser 102 prior to entering the fiber bundle 104. In some embodiments, each separated fiber 108-1 can have the same and/or nearly the same irradiance. That is, the light from the incident laser 102 that is incident upon each fiber within the fiber bundle 104 can have the same irradiance transferred to each separated fiber 108-1 coupled to the preparation cell 106.

In some embodiments, the preparation cell 106 can include an EOM coupled to each of the number of separated fibers 108-1 instead of a single EOM coupled to the incident laser 102. In these embodiments, the EOM coupled to each of the number of separated fibers 108-1 can be utilized to prepare the state of the light from the incident laser 102 of each of the separated fibers 108-1. In these embodiments, the EOM coupled to each of the number of separated fibers 108-1 can be a 2.1 GHz EOM and the incident laser 102 can be a state preparation laser or similar light source. That is, the preparation cell 106 can be used for laser cooling, state preparation, or a number of other processes that may require specifically prepared laser sources.

In some embodiments, the preparation cell 106 can include an acousto-optic modulator (AOM) coupled to each of the separated fibers 108-1. The AOM can be utilized to shutter (e.g., alternate between allowing the light through and not allowing the light through the preparation cell 106) the laser light from each of the separated fibers 108-1. In some embodiments, the AOM can be utilized for signal modulation and frequency control of the laser light passing through the separated fibers 108-1. In some embodiments, a radio frequency switch (RF switch) and/or microwave switch can be utilized to control light leakage that can be caused by the AOM shutter.

In some embodiments, the preparation cell 106 can include a device to set the beam polarization, such as a Pockels cell, that can be coupled to the AOM. The Pockels cell can include a voltage controlled wave plate (e.g., half-wave plate, quarter-wave plate, etc.). In some embodiments, the Pockels cell can be utilized to set a polarization of the laser light passing through the separated fibers 108-1 to a particular polarization (e.g., vertical, horizontal, combination, etc.).

The light from the incident laser 102 can be coupled to the EOM 122 and/or the fiber bundle 104 to pass light through a plurality of separated fibers 108-1 into the preparation cell 106 to prepare a state of the light from the incident laser 102. After exiting the preparation cell 106, the separated fibers 108-2 can be coupled to a vacuum port fiber bundle 110 that is coupled to an alignment cell 112. That is, the plurality of fibers coupled to the fiber bundle 104 are separated into separate fibers 108-1 before entering the preparation cell 106 and the separated fibers 108-2 after the preparation cell 106 are coupled to the vacuum port fiber bundle 110. Although the embodiment illustrated in FIG. 1 includes four fibers, embodiments of the present disclosure are not limited to a particular number of fibers.

The vacuum port fiber bundle 110 can maintain a vacuum within the alignment cell 112 while allowing the separated fibers 108-2 to be coupled to the alignment cell 112. The alignment cell 112 can utilize each of the separated fibers 108-2 to focus the corresponding laser light from each of the separated fibers 108-2 on an ion trap to allow the laser light of a particular separated fiber 108-2 to illuminate a particular ion that is trapped in a particular ion trap within the alignment cell 112. Previous systems and methods could require an additional number of lasers for each additional ion trap. In contrast, the system 100 can simultaneously utilize a single incident laser 102 to focus laser light onto a plurality of different ion traps simultaneously. In addition, the light of each separated fiber 108-2 can have a particular state that was prepared by the preparation cell 106.

When an ion within an ion trap is illuminated by the laser light from the light provided by the separated fibers 108-2 the ion can fluoresce light that can be captured by a number of fibers within the alignment cell 112 that are coupled to the vacuum port fiber bundle 110. The fluoresced light from the number of ions in the ion traps can be received at a detection cell 114 via a number of fibers 108-3. In some embodiments, the detection cell 114 can be outside the vacuum of the alignment cell 112 to reduce a quantity of space that is under vacuum. The detection cell 114 can be utilized to receive and quantify a time and brightness of the fluoresced light from the number of ions in the ion trap.

The system 100 can be utilized to prepare light from an incident laser 102 utilizing a plurality of tracks (e.g., EOM, AOM, Pockels cell, etc.) within the preparation cell 106 to address a plurality of ions. The quantity of ions that a single laser can address utilizing the system 100 can be determined by a number of factors. The number of factors can include, but is not limited to: a power of the illuminating laser, the power required at the ion, and/or a loss due to the components within the system (e.g., preparation cell 106, alignment cell 112, detection cell 114, EOM, AOM, Pockels cell, etc.). In some embodiments, the preparation cell 106 can be a main cause of light loss.

The system 100 can be utilized to individually address a relatively large number of ions while minimizing the number of lasers that need to be utilized. The system 100 can utilize a preparation cell 106 to receive a number of separated fibers 108-1 with light from an incident laser 102. The plurality of separated fibers 108-1 can be coupled to the preparation cell 106 via a number of tracks. The preparation cell 106 can simultaneously prepare a state (e.g., frequency, shuttering, etc.) of the received light from each of the separated fibers 108-1 and provide the prepared light state to an alignment cell 112. That is, the preparation cell 106 can allow control over each of the separated fibers 108-1 prior to entering the alignment cell 112. Thus, a single laser can be utilized to act as a number of different light sources for the alignment cell 112 and minimize the number of lasers needed to simultaneously feed a plurality of ion traps with laser light.

Figure 2:
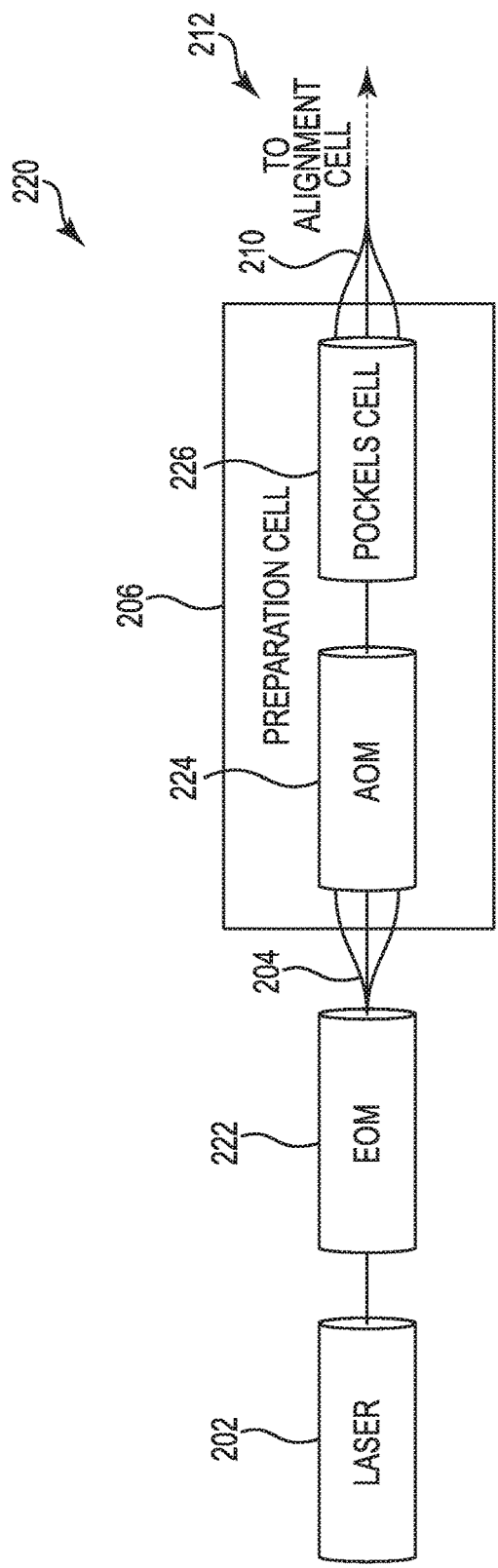
FIG. 2 illustrates an example of a preparation cell system in accordance with one or more embodiments of the present disclosure.

FIG. 2 illustrates an example of a preparation cell system 220 in accordance with one or more embodiments of the present disclosure. The preparation cell system 220 can be one example embodiment of a preparation cell system 100 as referenced in FIG. 1. The preparation cell system 220 can include a light source such as a laser 202. In some embodiments, the system 220 can utilize a Doppler cooling (DC) laser 202.

The laser 202 can be coupled to an electro-optical modulator (EOM) 222. In some embodiments, the EOM 222 can be a 7.37 GHz EOM that is coupled between the laser 202 and a fiber bundle. That is, the EOM 222 can be utilized to prepare a state of the laser 202 prior to the light from the laser 202 being received at a fiber bundle (e.g., fiber bundle 104 as referenced in FIG. 1, not shown in FIG. 2). A fiber bundle can receive light whose state has been prepared by the EOM 222 and split the light via a plurality of separated fibers (e.g., separated fibers 108-1 as referenced in FIG. 1, etc.).

The plurality of separated fibers can be coupled to a preparation cell 206. The preparation cell can include a number of tracks comprising an AOM 224 and/or a Pockels cell 226. For example, the preparation cell 206 can include an AOM 224 coupled to each of the separated fibers coupled to the preparation cell 206. In some embodiments, the AOM 224 can be utilized to set a frequency of the received laser light and/or shutter the received laser light. In some embodiments, the AOM 224 can be a 200 MHz AOM. In some embodiments, a radio frequency switch (RF switch) and/or microwave switch can be utilized to control light leakage that can be caused by the AOM 224 shutter.

The AOM 224 that is coupled to each of the plurality of separated fibers can be coupled to a Pockels cell 226. As described herein, the Pockels cell 226 can be utilized to set a polarization of the laser light passing through the separated fibers. The plurality of fibers from the preparation cell can be coupled to an alignment cell 212 (e.g., alignment cell 112 as referenced in FIG. 1) via a vacuum port fiber bundle 210 (e.g., vacuum port fiber bundle 110 as referenced in FIG. 1).

Figure 3:
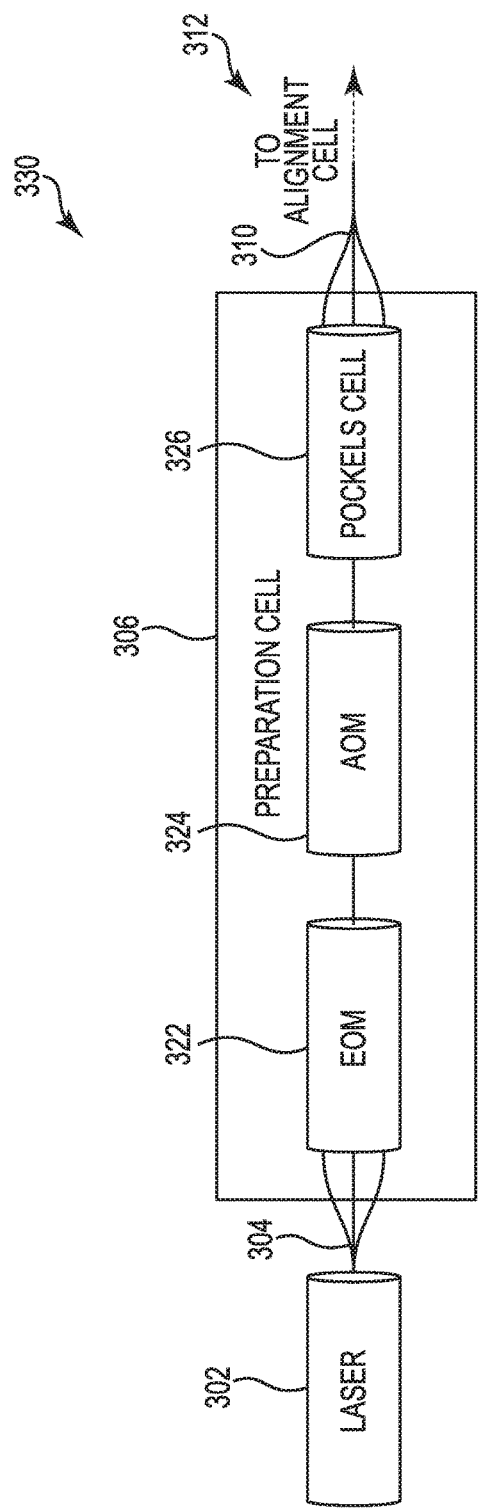
FIG. 3 illustrates an example of a preparation cell system in accordance with one or more embodiments of the present disclosure.

FIG. 3 illustrates an example of a preparation cell system 330 in accordance with one or more embodiments of the present disclosure. The preparation cell system 330 can be one example embodiment of a preparation cell system 100 as referenced in FIG. 1. The preparation cell system 330 can include a light source such as a laser 302. In some embodiments, the system 330 can include a quantum operation (QO) laser 302.

The laser 302 can be coupled to a fiber bundle (e.g., fiber bundle 104 as referenced in FIG. 1, not shown in FIG. 3). The fiber bundle 304 can be utilized to receive light from the laser 302 and split the light from the laser 302 into a plurality of separated fibers. Each of the separated fibers can be coupled to the preparation cell 306. The preparation cell can include a number of tracks comprising an EOM 322, an AOM 324, and a Pockels cell 326 coupled to each separated fiber.

Each of the separated fibers can be first coupled to an EOM 322 within the preparation cell 306. The EOM 322 can be utilized to prepare the state of the laser light of each of the separated fibers. The EOM coupled to each of the number of separated fibers can be a 2.1 GHz EOM.

The preparation cell 306 can include an AOM 324 coupled to each of the separated fibers and corresponding EOM 322 coupled to the preparation cell 306. In some embodiments, the AOM 324 can be utilized to set a frequency of the received laser light and/or shutter the received laser light. In some embodiments, the AOM 324 can be a 200 MHz AOM. In some embodiments, a radio frequency switch (RF switch) and/or microwave switch can be utilized to control light leakage that can be caused by the AOM 324 shutter.

The AOM 324 that is coupled to each of the plurality of separated fibers can be coupled to a Pockels cell 326. As described herein, the Pockels cell 326 can be utilized to set a polarization of the laser light passing through the separated fibers. The plurality of fibers from the preparation cell can be coupled to an alignment cell 312 (e.g., alignment cell 112 as referenced in FIG. 1) via a vacuum port fiber bundle 310 (e.g., vacuum port fiber bundle 110 as referenced in FIG. 1).

The system 330 can be utilized to individually address a relatively large number of ions while minimizing a number of QO lasers that need to be utilized. The system 330 can utilize a preparation cell 306 to receive a number of separated fibers with light from an incident laser 302. The preparation cell 306 can simultaneously prepare a state of the received light from each of the separated fibers and provide the prepared light state to an alignment cell 312. In some embodiments, the system 330 can be utilized to set and interrogate ytterbium's hyperfine states. Thus, a single laser can be utilized to act as a number of different light sources for the alignment cell 312 and minimize the number of lasers needed to simultaneously feed a plurality of ion traps with laser light.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above elements and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A preparation cell system, comprising:
a laser coupled to a fiber bundle comprising a plurality of fibers, wherein the fiber bundle separates the plurality of fibers that are utilized for a plurality of ion traps;
a preparation cell comprising a plurality of electro-optical modulators (EOMs) to prepare a state of laser light received by the fiber bundle, wherein the state of laser light is prepared by at least one of setting a frequency, setting a polarization, or shuttering the laser light passing through each of the separated fibers, wherein each respective EOM is coupled to a different one of the plurality of fibers separated by the fiber bundle; and
a vacuum port fiber bundle coupled to an alignment cell to receive the plurality of fibers.

2. The system of claim 1, comprising a plurality of acousto-optical modulators (AOMs), wherein each respective AOM is coupled to a different one of the plurality of EOMs.

3. The system of claim 2, comprising a plurality of Pockels cells, wherein each respective Pockels cell is coupled to a different one of the plurality of AOMs.

4. The system of claim 1, wherein light received by each of the plurality of fibers from the laser is individually shuttered and prepared prior to entering the vacuum port fiber bundle.

5. The system of claim 1, comprising an RF switch coupled to the plurality of AOMs to control light leakage from an AOM shutter.

6. The system of claim 4, wherein the laser performs an operation other than laser cooling.

7. A preparation cell system, comprising:
a laser coupled to a plurality of electro-optical modulators (EOMs);
a fiber bundle comprising a plurality of fibers coupled to the plurality of EOMs, wherein the fiber bundle separates the plurality of fibers that are utilized for a plurality of ion traps;
a preparation cell comprising the plurality of EOMs to prepare a state of laser light received by the fiber bundle, wherein the state of laser light is prepared by at least one of setting a frequency, setting a polarization, or shuttering the laser light passing through each of the separated fibers, wherein each respective EOM is coupled to a different one of the plurality of fibers separated by the fiber bundle; and
a vacuum port fiber bundle coupled to an alignment cell to receive the plurality of fibers.

8. The system of claim 7, comprising a plurality of acousto-optical modulators (AOMs) couples to each of the plurality of fibers.

9. The system of claim 8, comprising a plurality of Pockels cells, wherein each respective Pockels cell is coupled to a different one of the plurality of AOMs.

10. The system of claim 7, wherein the vacuum port fiber bundle maintains a vacuum within an alignment cell while allowing the plurality of fibers to be coupled to the alignment cell.

11. The system of claim 10, wherein the alignment cell utilizes each of the plurality of fibers to focus the corresponding laser light of a particular plurality of fibers on an ion trap to allow the laser light of the particular plurality of fibers to illuminate a particular ion.

12. The system of claim 11, wherein the particular ion is trapped in a particular ion trap within the alignment cell.

13. The system of claim 7, wherein the laser is the same diameter as the fiber bundle to avoid light from the laser from escaping an exterior portion of the fiber bundle.

14. A preparation cell system, comprising:
a laser coupled to an electro-optical modulator (EOM);
a fiber bundle comprising a plurality of fibers coupled to the EOM, wherein the fiber bundle separates the plurality of fibers that are utilized for a plurality of ion traps;
a preparation cell comprising the EOM to prepare a state of laser light received by the fiber bundle, wherein the EOM is coupled to the plurality of fibers separated by the fiber bundle to:
set a frequency and polarization of laser light received by the plurality of fibers from the EOM; and
shutter the laser light received by the plurality of fibers from the EOM; and
a vacuum port fiber bundle coupled to an alignment cell.

15. The system of claim 14, wherein the EOM generates spacing sidebands from light emitted by the laser.

16. The system of claim 14, comprising a plurality of acousto-optical modulators (AOMs) coupled to each of the plurality of fibers.

17. The system of claim 16, comprising a plurality of Pockels cells, wherein each respective Pockels cell is coupled to a different one of the AOMs, wherein each of the plurality of Pockels cells are coupled to the vacuum port fiber bundle.

18. The system of claim 14, wherein the laser is a cooling laser.

19. The system of claim 18, wherein the cooling laser is a Doppler cooling (DC) laser.

20. The system of claim 14, wherein the EOM generates spacing sidebands for each of the plurality of fibers.

* * * * *